United States Patent [19]

McClallen

[11] Patent Number: 5,232,002
[45] Date of Patent: Aug. 3, 1993

[54] DENTAL FLOSSING APPARATUS

[76] Inventor: Steven L. McClallen, R.R. 2, Box 210, Eureka, Ill. 61530

[21] Appl. No.: 896,670

[22] Filed: Jun. 10, 1992

[51] Int. Cl.[5] .......................................... A61C 15/00
[52] U.S. Cl. .................................. 132/325; 132/324; 132/323
[58] Field of Search ............... 132/323, 324, 325, 326, 132/327; 433/31

[56] References Cited

U.S. PATENT DOCUMENTS

| | | | |
|---|---|---|---|
| 1,110,680 | 9/1914 | Gamble | 132/325 |
| 2,354,454 | 7/1944 | Geffner | 132/91 |
| 2,492,291 | 12/1949 | Johnson | 132/324 |
| 2,873,749 | 2/1959 | Gjerde | 132/323 |
| 3,236,247 | 2/1966 | Brockman | 132/91 |
| 3,421,524 | 1/1969 | Waters | 132/92 |
| 3,828,804 | 8/1974 | Ely | 132/91 |
| 3,910,294 | 10/1975 | Reed | 132/91 |
| 4,164,814 | 8/1979 | Klostermark | 433/31 |
| 4,192,330 | 3/1980 | Johnson | 132/91 |
| 4,338,957 | 7/1982 | Meibauer | 132/91 |
| 4,404,978 | 9/1983 | Withers | 132/323 |
| 4,458,702 | 7/1984 | Grollimund | 132/322 |
| 4,586,521 | 5/1986 | Urso | 132/92 R |
| 4,637,412 | 1/1987 | Martinez | 132/92 R |
| 4,807,651 | 2/1989 | Naydich | 132/323 |
| 4,827,952 | 5/1989 | Kos | 132/323 |
| 5,060,681 | 10/1991 | Westbrook et al. | 132/323 X |
| 5,105,840 | 4/1992 | Giacopuzzi | 132/325 |

FOREIGN PATENT DOCUMENTS 0644176  5/1928  France ................ 132/323

Primary Examiner—John J. Wilson
Assistant Examiner—Nicholas D. Lucchesi
Attorney, Agent, or Firm—Charles E. Lanchantin, Jr.

[57] ABSTRACT

A dental flossing apparatus includes a body having a gripping portion and a bifurcated distal portion defining a pair of tines and a slot between them, and a rocker member pivotally connected to the body. The opposite ends of a strand of dental floss are so connected to the body and/or rocker member that the user can selectively rock the rocker member and cause an intermediate portion of the dental floss to be reciprocated between the guiding tines for better cleaning the facing surfaces of adjacent teeth.

26 Claims, 8 Drawing Sheets

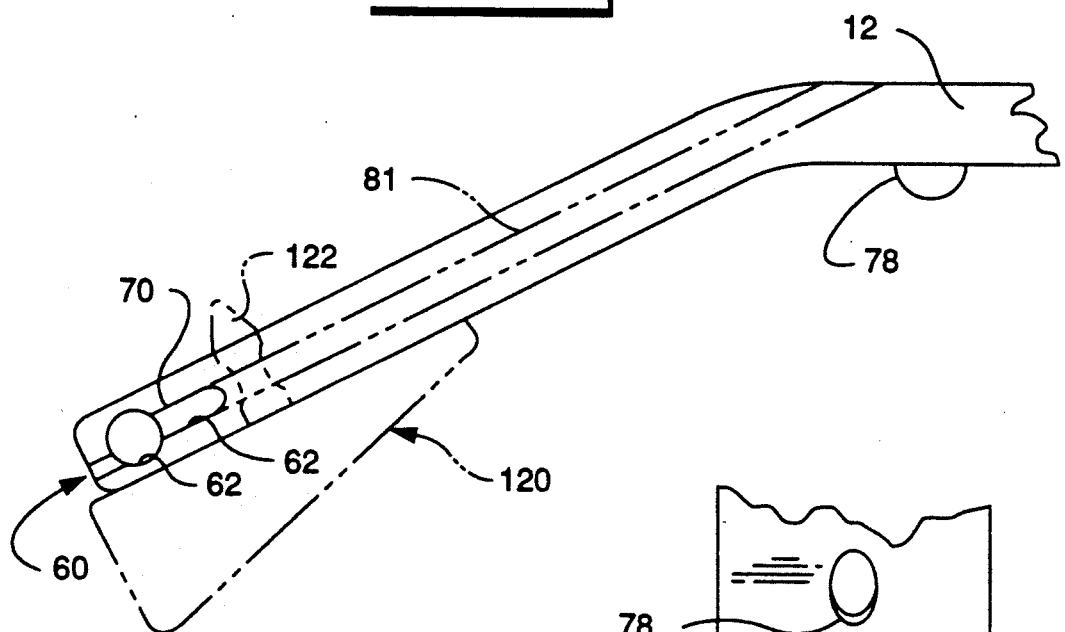
Fig_2_
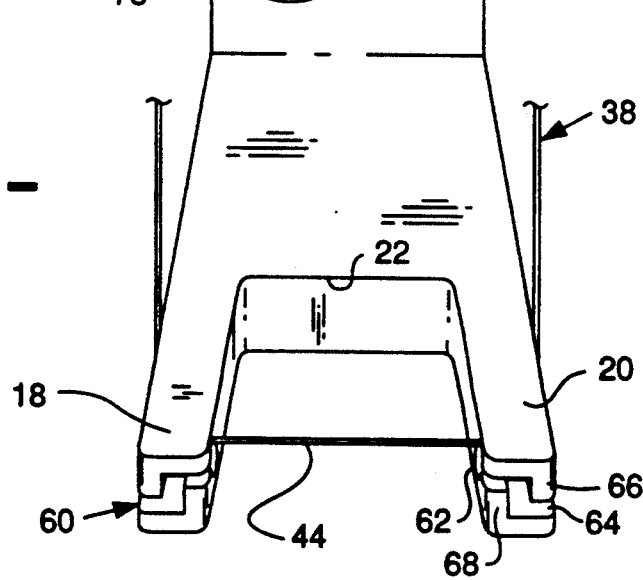
Fig_3_

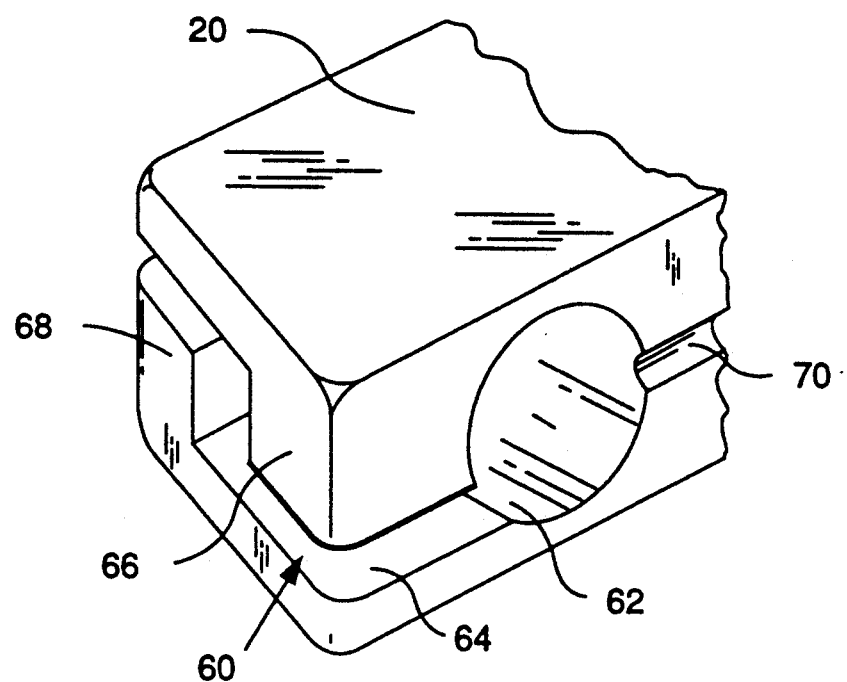
Fig_6_
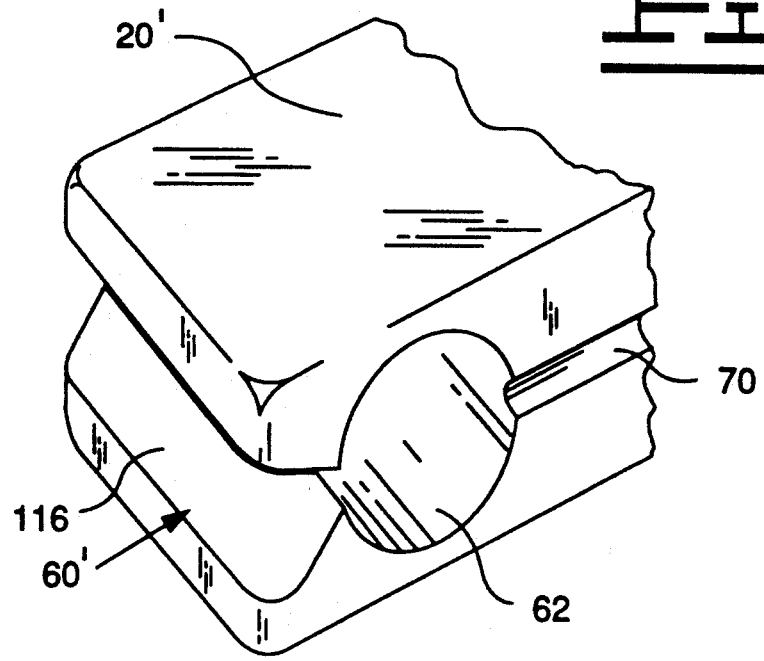
Fig_7_

Fig_8_
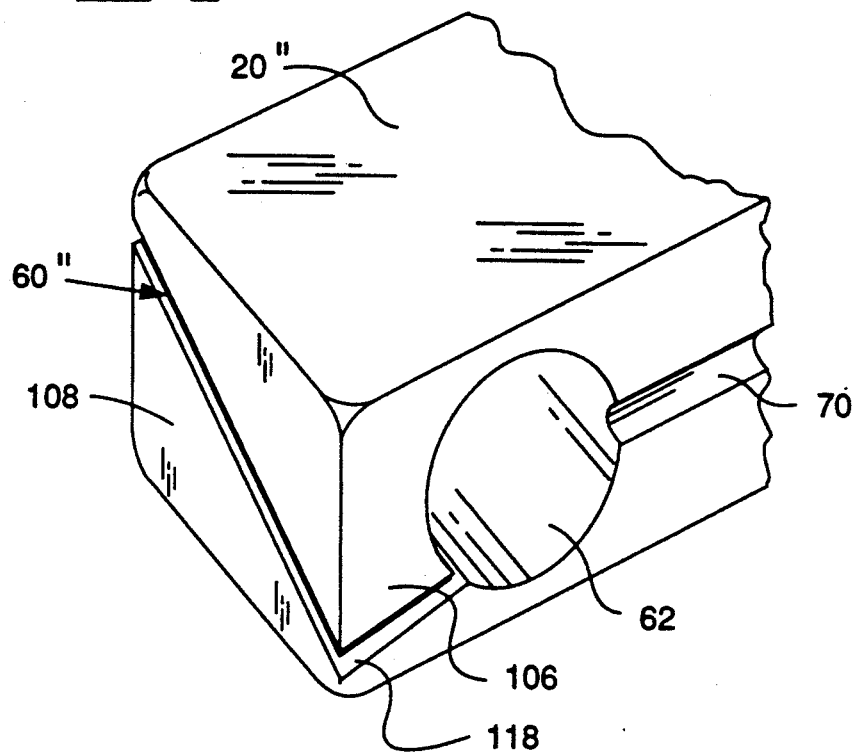
Fig_9_
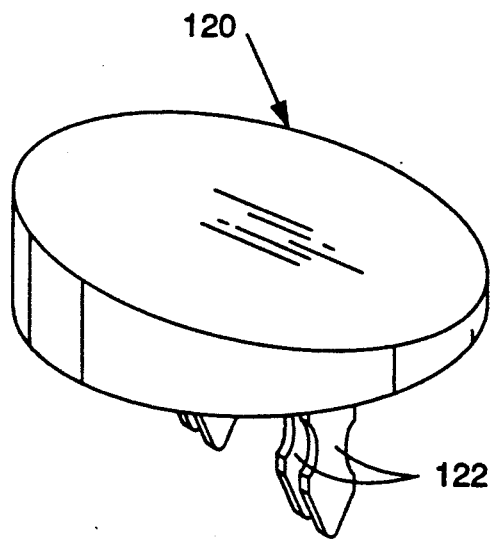

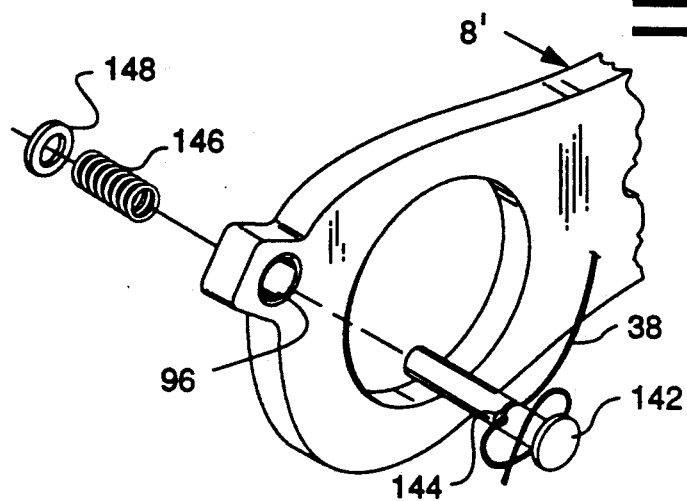
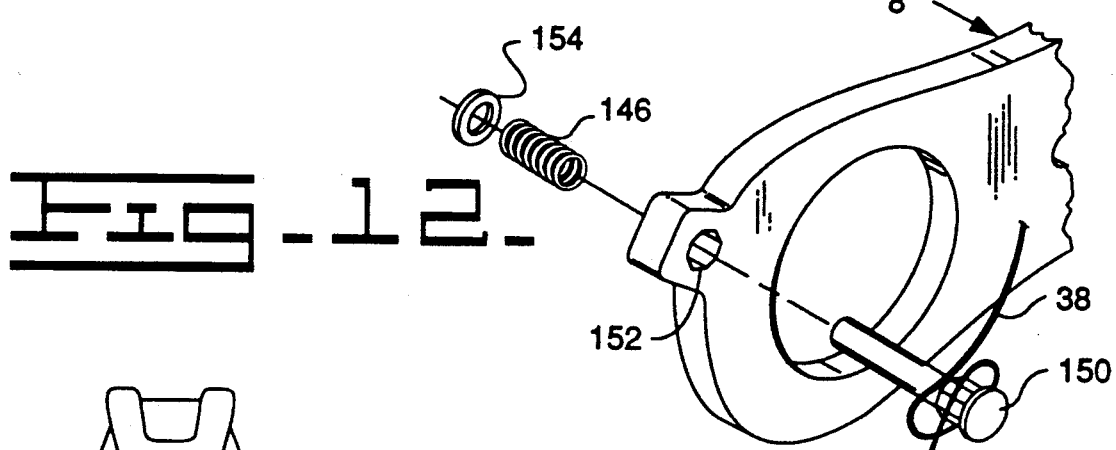
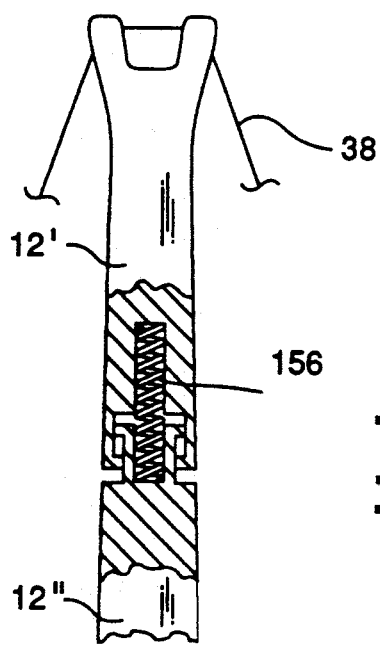

DENTAL FLOSSING APPARATUS

TECHNICAL FIELD

This invention relates generally to a dental flossing apparatus which is hand-held and is used to clean between the teeth, and more particularly to an apparatus for controlled tensioning and controlled reciprocating movement of the floss between the teeth, and including certain elements to better see the flossing area and a storage case for the apparatus.

BACKGROUND ART

Dental floss has long been recognized as an effective way to remove debris from between the teeth, and plaque from the interdental tooth surfaces between adjacent teeth. Dental plaque is a coating on the teeth of a complex bacterial nature which when not removed can lead to the formation of tooth decay, gingivitis, and further periodontal disease with the eventual deterioration of gum and bone tissue. Of course, a tooth brush is widely used for scrubbing teeth and removing plaque on tooth surfaces struck by the bristles. However, it is not very effective in removing plaque on the surfaces between adjacent teeth, and is often totally unable to dislodge material stuck between the teeth.

Flossing the teeth is commonly accomplished by wrapping a length of dental floss around the index finger of the left and right hands and inserting one or both of these fingers into the mouth in order to slip the dental floss between the teeth. This method has several disadvantages:

1. Inserting the fingers into the mouth can be unsanitary;
2. Inserting fingers into the mouth can obstruct the view of the teeth area to be cleaned;
3. Large fingers can make complete cleaning impossible;
4. The molars are very hard to floss even with smaller fingers;
5. Proper flossing action is often difficult to achieve;
6. The floss tends to slip off of the fingers and tight wrapping of the floss on the fingers can lead to discomfort;
7. Excessive length of dental floss is used to avoid the slipping problem.

Due to such difficulties, many dental floss holders have been designed. Most of them have a pair of parallel arms or legs at the distal end thereof and eyelets or grooves for guiding the floss between the legs. U.S. Pat. No. 3,910,294 issued Oct. 7, 1975 to D. C. Reed includes a pivotal device to tighten the floss, but no way of reciprocating the floss. That patent also requires a loop of floss that must be measured. U.S. Pat. No. 4,827,952 issued May 9, 1989 to P. Kos discloses a pair of spreadable flosser arms that maintain tension on special beaded floss. U.S. Pat. No. 4,192,330 issued to G. D. Johnson on Mar. 11, 1980 illustrates a pair of deflectable arms formed on a holder for an expandable floss cartridge. U.S. Pat. No. 3,828,804 issued to R. N. Ely on Aug. 13, 1974, provides for one-time tensioning of a loop of floss between the arms thereof, and has a very limited tensioning range.

Some dental flossing devices have been motorized, such as those represented by U.S. Pat. Nos. 3,421,524 issued Jan. 14, 1969 to W. A. Waters and U.S. Pat. No. 4,338,957 issued Jul. 13, 1982 to R. H. Meibauer. These patents illustrate bifurcated heads that oscillate the dental floss fixed thereto through a small arc. They are basically attachments to an electrically powered tooth brush holder, and are not only excessively bulky and uneconomical, but also are awkward and uncomfortable because the arms continually oscillate at either side of the tooth being cleaned.

U.S. Pat. No. 4,586,521 issued May 6, 1986 to C. L. Urso discloses an extremely complex and bulky dental flosser with movable inner fork tines disposed between shielding outer fork tines. The inner fork tines move up and down while a spool drive mechanism causes the dental floss to be pulled in one direction between the spanning tines. By using a trigger, the operator can apparently start, stop, and control the speed of an electric motor and a brake associated with the dispensing spool. This flosser is awkward to use and consumes considerable dental floss.

Basically, such motorized flossers are overly complex and difficult to use, and lack the ability to truly simulate the back-and-forth movement of the index fingers. Thus, what is needed is a dental flossing apparatus that:
(a) is compact;
(b) is easily manipulated by one hand;
(c) provides for reciprocating action of the dental floss through the bifurcated flosser head for improved and quicker scrubbing of the teeth;
(d) provides for controlled reciprocation of the dental floss when desired under the control of one or two fingers;
(e) provides for quick and easy changing and for anchoring of the dental floss;
(f) is economical to manufacture;
(g) preferably provides for manual control of the floss tension during use; and
(h) preferably provides an improved way of seeing precisely where the dental floss is to be inserted and operated between adjacent teeth.

The present invention is directed to overcoming one or more of the problems as set forth above.

DISCLOSURE OF THE INVENTION

In one aspect of the present invention there is provided a dential flossing apparatus for cleaning teeth by supporting a length of dental floss, and including an elongate body having a distal portion defining a pair of tines and a slot between them, and a rocker member rockably connected to the body. The dental flossing apparatus further includes a first device for pulling a first end of the floss in response to pivotal movement of the rocker member, and a second device for reacting to the pulling of the first end at a second end of the floss and for pulling the second end with pivotal movement of the rocker member in the opposite direction to allow reciprocating movement of the dental floss between the tines with manually controlled reciprocation movement of the rocking member.

In accordance with a further aspect of the invention a dental flossing apparatus is provided including a shaft having a bifurcated distal portion defining a of tines for spanningly receiving the intermediate portion of a length of dental floss, and an intermediate portion. A rocker member having first and second arms is pivotally connected to the intermediate portion of the shaft by a coupling assembly, and anchoring devices are connected to the arms and to the opposite ends of the floss such that the user can manually rock the rocker member and cause reciprocation of the intermediate portion of the dental floss between the tines for better cleaning of the facing surfaces between adjacent teeth.

In a still further aspect of the invention, a dental flossing apparatus includes a body defining a distal portion having a pair of tines and a slot between them, and an intermediate portion. A rocker member has a central part and first and second arms extending from the central part which are respectively connected to the opposite ends of a length of dental floss. A first coupling device provides for pivotal movement of the central part of the rocker member on the intermediate while a second coupling device provides for extended movement between the rocker member and the distal portion of the body and thereby controlled tensioning of the dental floss between the tines.

Preferably, the rocker member has finger-receiving apertures permitting it to be reciprocated easily with the index and ring fingers. Arms on the rocker member are connected to the dental floss, so that as it is rocked back and forth the dental floss is reciprocated also. A lockable spool assembly can be used for connecting one end of the floss to the body or rocker assembly.

BRIEF DESCRIPTION OF THE DRAWINGS

FIG. 2 is an enlarged, fragmentary and diagrammatic side view of the distal end of the dental flossing apparatus of FIG. 1.

FIG. 3 is an enlarged, fragmentary and diagrammatic perspective view of the bifurcated distal portion of the dental flossing apparatus of FIG. 1.

FIG. 6 is an enlarged, fragmentary perspective view of the tip of the tine illustrated in FIG. 3.

FIG. 7 is an enlarged, fragmentary perspective view of a modification of the tine tip shown in FIG. 6.

FIG. 8 is an enlarged, fragmentary view of a further modification of the tine tips illustrated in FIGS. 6 and 7.

FIG. 9 is a diagrammatic perspective view of a mirror which can be used as an attachment to the bifurcated distal portion of the dental flossing apparatus as is shown in phantom outline in FIG. 2.

FIG. 11 is an enlarged exploded perspective view of an alternate floss anchoring pin located on the rocking member of FIG. 5.

FIG. 12 is an enlarged exploded perspective view of a modified floss anchoring pin of FIG. 11.

FIG. 13 is a diagrammatic, fragmentary view of a modified shaft showing the intermediate portion thereof in partial cross section and as being in two telescoping parts with a compression spring therebetween.

DETAILED DESCRIPTION OF THE PREFERRED EMBODIMENT

Figure 1:
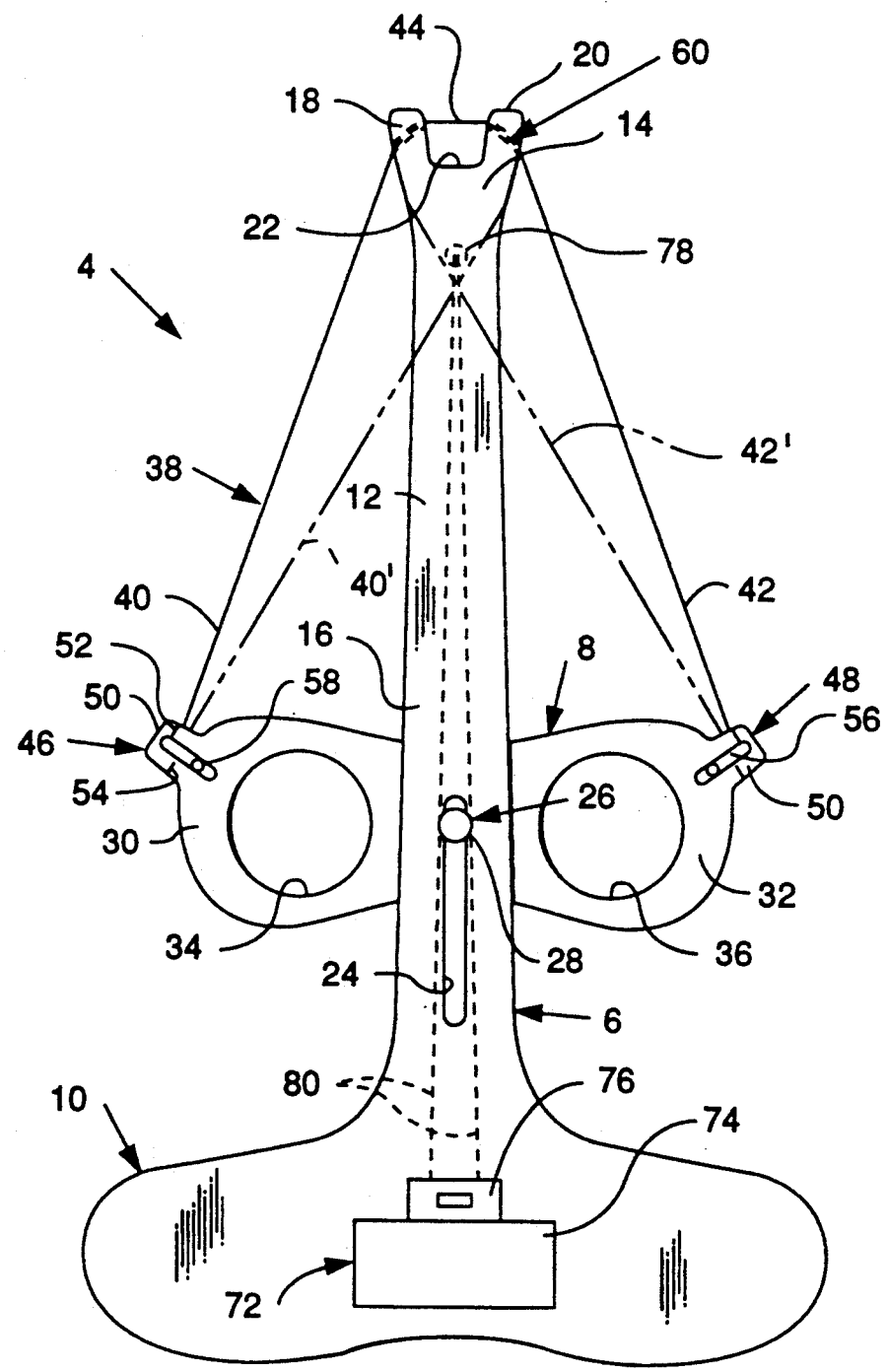
FIG. 1 is a diagrammatic plan view of a dental flossing apparatus constructed in accordance with one embodiment of the present invention.

Referring to FIG. 1, there is shown a dental flossing apparatus 4 including an elongate body 6 and a finger-operated rocker member 8 movably connected to the body. The body 6 defines a proximal gripping portion or handle 10 suitably formed to fit the right or left hand of the average user. The body further includes a relatively flat shaft 12 extending approximately perpendicular to the handle 10 which has a bifurcated distal portion or head 14, and an intermediate portion 16 located between the handle and the distal portion. As shown in FIG. 2 the bifurcated distal portion 14 is preferably angled downwardly and away from the relatively planar remainder of the shaft 12. As is shown in FIGS. 1 and 3 the bifurcated distal portion defines a pair of blunted tines 18 and 20, and a tooth-receiving slot 22 therebetween of a sufficient size to receive a large molar. For example, the slot illustrated is approximately 1.3 centimeters wide and 1 centimeter deep. In the embodiment illustrated the shaft 12 is about 0.4 centimeters thick, 17 centimeters long, and is convergingly tapered toward the distal portion so that at its widest point it is somewhat less than 3 centimeters and at its narrowest point is about 1 centimeter.

An elongate aperture 24 is defined in the intermediate portion 16 of the shaft 12, and coupling means 26 are provided for movably securing the rocker member 8 to the shaft. The coupling means shown in FIG. 1 includes a pin or rivet 28 provided with an enlarged head relative to the width of the aperture 24. This pin is suitably secured to the rocker member. The rocker member is preferably made of the same plastic material as the body 6, and has planar upper and lower surfaces spaced in parallel relation about 0.4 centimeters apart. The upper flat surface of shaft 12 is also flat for better stability when rocker member 8 is adjacently disposed to it. As shown in FIG. 1, the rocker member 8 has first and second arms 30 and 32 that extend in a perpendicular manner oppositely away from the shaft 12 at the coupling means 26. The first arm 30 defines an aperture 34, and the second arm 32 defines an aperture 36 which are of a size sufficient to receive a persons fingers therein.

A length of conventional dental floss 38 has a first end 40, a second end 42, and an intermediate portion 44. As is illustrated in FIG. 1, the first end 40 is releasably secured to the outer end of the first arm 30 of the rocker member 8 by first anchoring means 46. The second end 42 of the floss is similarly secured to the outer end of the second arm 32 by second anchoring means 48. As is illustrated, each anchoring means includes cleats 50 defined by oppositely disposed tapered slots 52 and 54 in the rocker member 8, and a retaining clip 56 pivotably secured to the rocker member by a rivet 58. Thus, the ends of the dental floss are wrapped around the cleats 50 in the tapered slots 52 and 54, and the clips 56 rotated into position over the floss for more positive retention.

As is shown in FIGS. 2, 3, and 6, a contoured aperture and guide slot 60 is defined at the outer ends of each of the blunted tines 18 and 20, and the intermediate portion 44 of the dental floss 38 is received therein. Each of the guide slots 60 includes a tubular aperture 62 and a zig-zag slit 64 that extends inwardly from the end of the tine to an intersecting relationship with the tubular aperture. Thus, it may be noted that the zig-zag slit 64 is defined in part by a downwardly extending tab 66 and a upwardly extending tab 68 when viewing FIGS. 3 and 6. A side groove 70 is preferably defined within the opposite sides of the bifurcated distal portion 14, and the outer edges of the aperture 62 are suitably rounded to promote less friction with the dental floss 38 as it changes direction from movement of the rocker member 8. The aperture 62 is also preferably inclined at an angle greater than 90 degrees, for example 135 degrees with respect to the side groove 70 to improve its transitional relationship with the anchored dental floss.

An optional lighting device 72 is diagrammatically illustrated in FIG. 1, and can be noted to include a battery 74, and a light bulb 78 connected to a switch 76 by electrical conductors or copper wires 80 embedded in the shaft 12.

One way of bringing the dental floss 38 closer to the shaft 12 at the distal portion 14 is to switch or reverse the positions of the floss ends 40 and 42 with respect to the opposite anchoring means 48 and 46 as is shown by the phantom lines in FIG. 1. In this way the floss crosses over the shaft and can follow an extended or elongate side groove 81 as is shown in phantom lines in FIG. 2. This narrows the area of the flossing apparatus that is inserted into the oral cavity, and reduces contact of the floss with the lips or cheeks.

Figure 4:
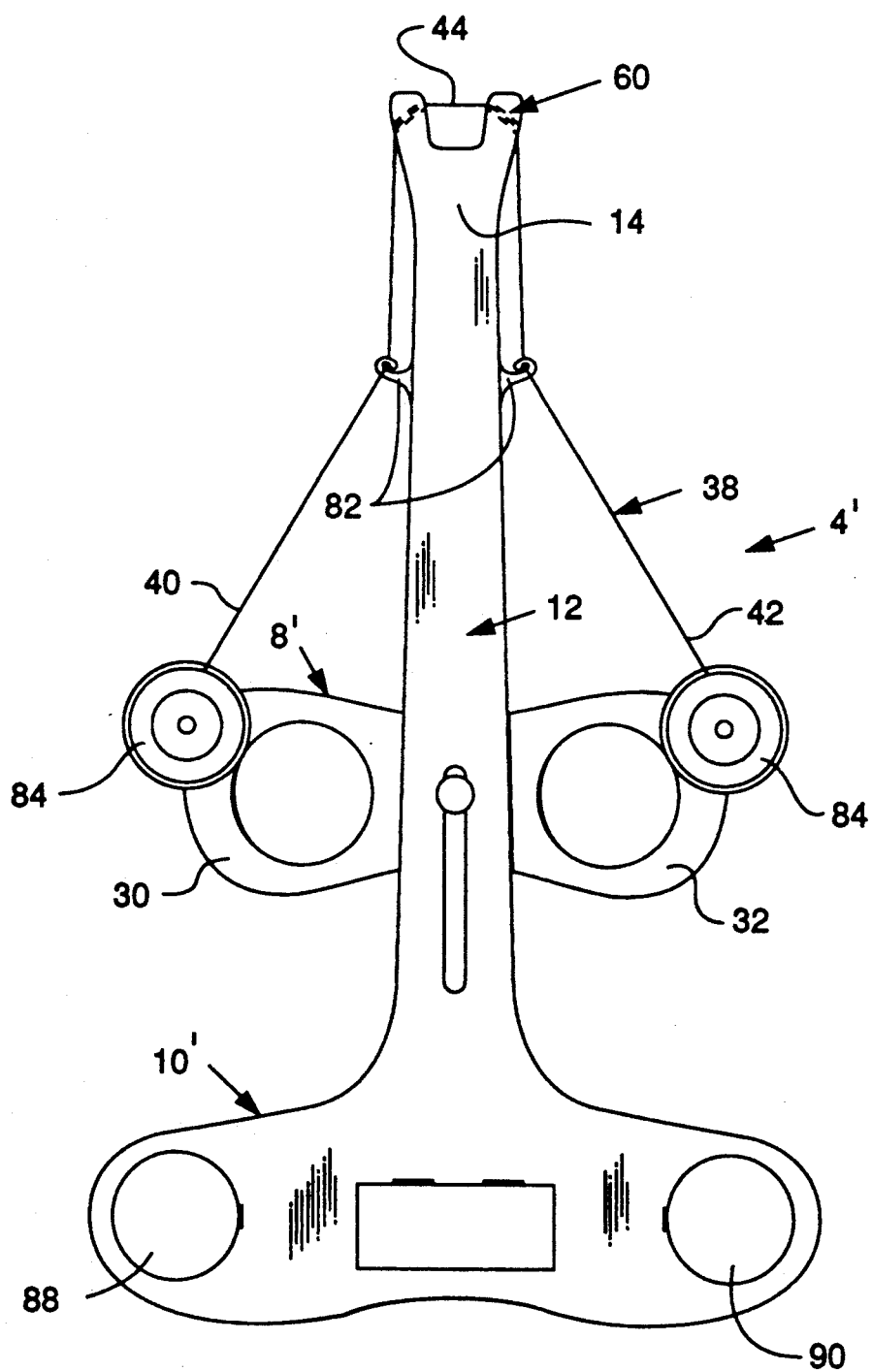
FIG. 4 is a diagrammatic plan view of another embodiment of the present invention.

FIG. 4 is an alternate embodiment dental flossing apparatus 4' that is very similar to the embodiment of FIGS. 1-3. However, a pair of floss guide hooks 82 have been added. These guide hooks can be an integrally molded portion of the shaft 12, and guide the dental floss 38 close to the shaft at the distal portion 14 so that floss interference with the sides of a persons mouth is reduced. The dental flossing apparatus 4' also includes a spool assembly 84 on each of the arms 30 and 32 at the outer ends of the rocker member 8. Preferably, one of the spool assemblies 84 is loaded with new dental floss material and the other is adapted to receive the used dental floss. An optional floss spool storage area or container 88 and a mirror storage area or container 90 are also shown on the handle 10'. These storage areas can consist of recesses within the handle with suitable lids.

Figure 5:
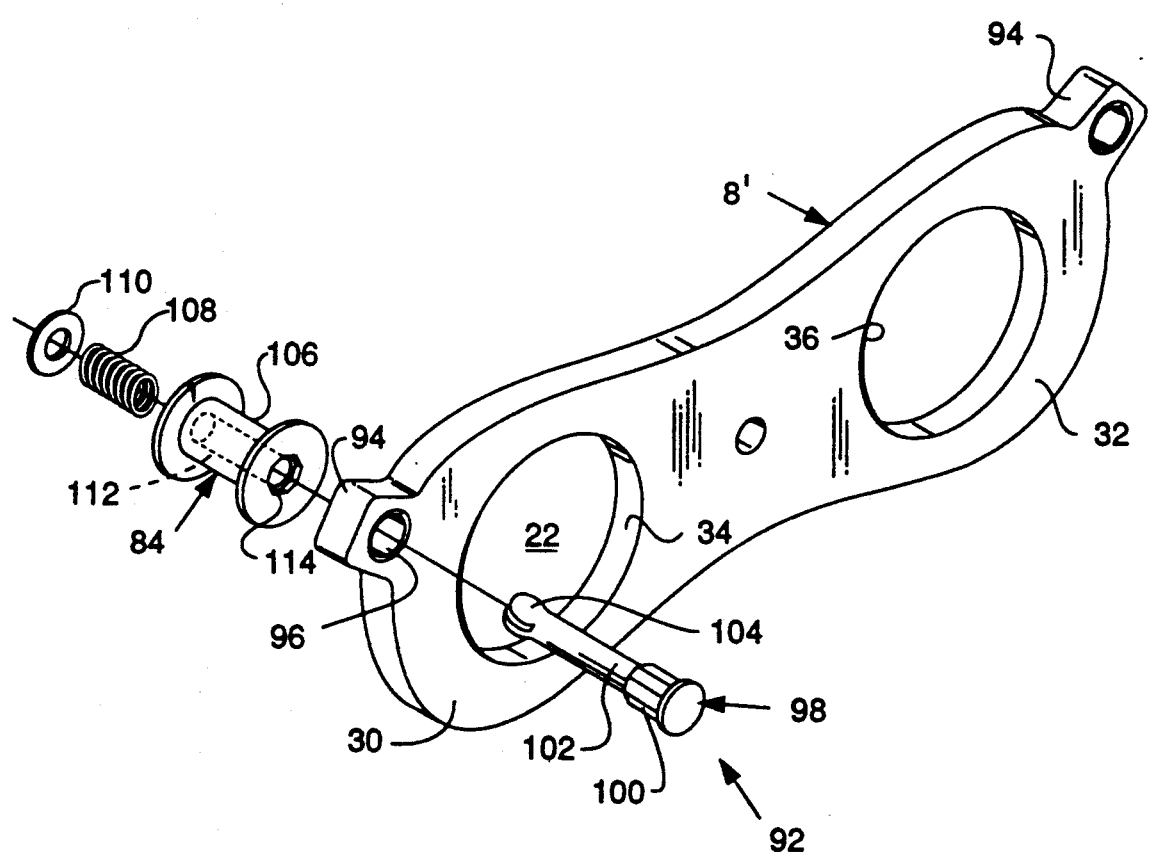
FIG. 5 is an enlarged exploded perspective view of the rocking member portion of the dental flossing apparatus illustrated in FIG. 4 showing certain details thereof.

FIG. 5 is an enlarged view of the alternate embodiment rocker member 8' illustrating mounting means 92 for releasably securing the spool assembly 84 to the arm 30. An integral tang 94 is located on the left side when viewing the drawing and defines a contoured bore 96 adapted to receive a pin 98. The pin 98 has a multi-sided or polygonal anchoring base 100, a cylindrical central portion 102, and a resilient split bulb end portion 104. The pin 98 provides a mounting post for receiving the spool assembly 84 including a spool 106, a compression spring 108, and a washer or retainer 110. The spool has a cylinder bore 112 and a polygonal locking portion 114 defined at one end thereof. The spool 106 is slipped over the pin 98 and the spring 108, and then the washer 110 is slipped over the resilient split bulb end portion 114 to retain the assembly together. Although only one spool assembly is shown in FIG. 5, another similar spool assembly is preferably incorporated on the opposite side of rocker member 8' to make a floss dispensing unit and a cooperating floss receiving unit. Although not shown in FIG. 5, dental floss 38 is wound around the left spool 106, threaded through the left guide hook 82 shown in FIG.4, the guide slots 60, the right guide hook 82, and to the right spool assembly 84.

FIG. 6 is an enlarged view of the tip of the tine 20. A contoured guide slot 60 is illustrated as a zig-zag slot 64 and defined by a upper tab 66 and a lower tab 68. Dental floss 38, when inserted into the zig-zag slot 64, is better retained in the tubular aperture 62. A side groove 70 is illustrated for the purpose of guiding the dental floss 38 along the tine 20.

FIG. 7 illustrates a variation of the contoured guide slot 60 shown in FIG. 6. The slot 60' differs in that a straight, beveled slit 116 has a wide opening at the front and tapers convergingly rearwardly until it opens into the aperture 62.

FIG. 8 is another variation contoured guide slot 60", wherein a diagonally slit 118 is provided. The slit 118 could be optionally wider than that illustrated, and even convergingly rearwardly tapered as is shown in FIG. 7 to facilitate loading the floss.

FIG. 9 is an enlarged illustration of a mirror 120 that can be releasably secured to the distal portion or head 14 of the shaft 12 shown in FIGS. 1 and 4. The mirror has spring-like retention clips 122 that can be slipped over the blunted tines 18 and 20 in the position illustrated by the phantom lines thereof in FIG. 2. The mirror can be stored in the handle 10 at the storage area 90 shown in FIG. 4.

Figure 10:
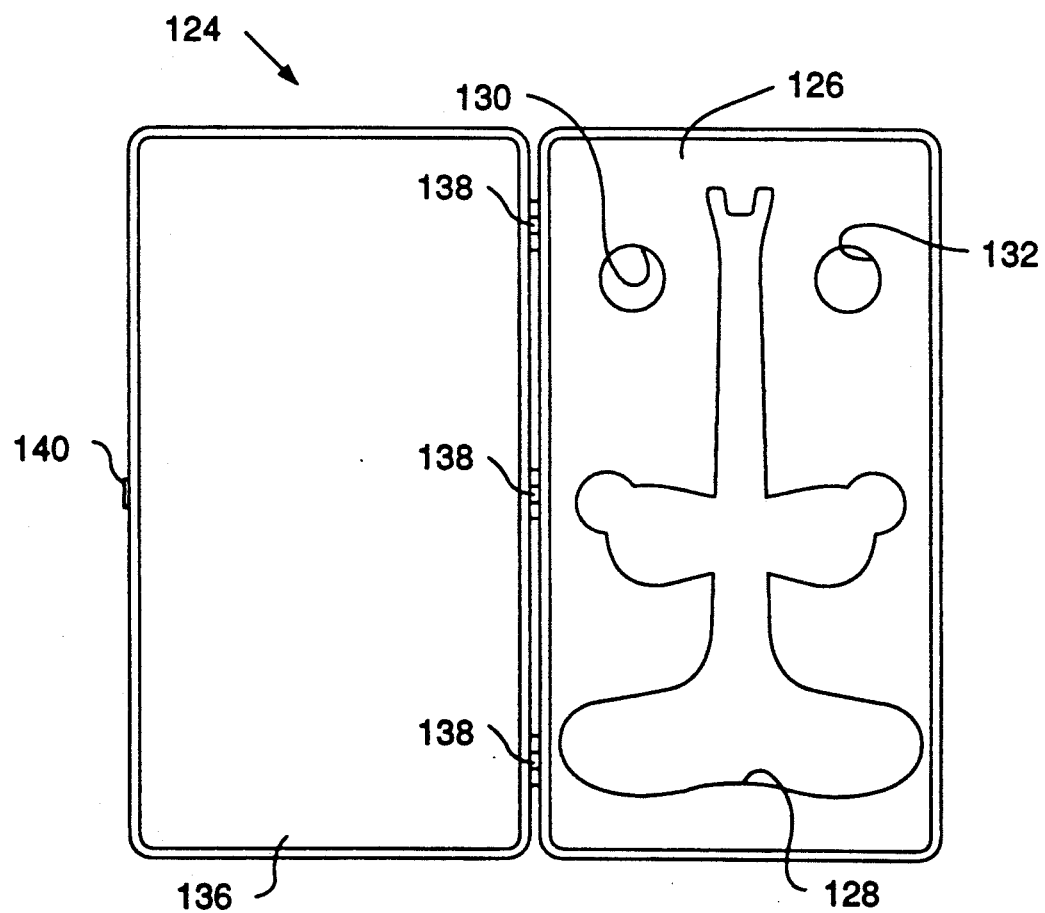
FIG. 10 is a plan view of an optional and opened hinged storage case for protecting the dental flossing apparatus of the present invention.

FIG. 10 is a diagrammatic illustration of a storage case 124 for carrying the dental flossing apparatus 4. The case includes a base 126 defining a recessed pocket 128 having a profile similar to that of the dental flossing apparatus. The base illustrated also has formed recesses 130 and 132 for the mirror 120 and spool 106, and a cover 136 is pivotally secured thereto by hinges 138. A suitable latch 140 enables the cover to be clamped to the base.

FIG. 11 is an enlarged exploded perspective view of an alternate floss anchoring pin 142 and a compression spring 146. The pin 142 is inserted through the bore 96 of the rocker member 8' the compression spring is slipped over the pin, acting between the retaining cap and the rocker member 8', and a retaining cap 148 is secured to the distal portion of the pin. The retaining cap end of the pin 142 is forceably moved by finger pressure and an indented portion 144 of the pin is exposed under the head of the pin 142 whereby a portion of dental floss 38 is wrapped around the pin 142 at the indentation 144. Finger pressure is released and the pin 142 retracts due to the compression of spring 146 and the floss wrapped indentation 144 is pulled within the upper and lower surface boundaries of the rocker member 8' and therefore secured.

FIG. 12 is an enlarged exploded perspective view of a modified flow anchoring pin. A multifaceted headed pin 150 is inserted into the multifaceted bore 152 of the rocker member 8' and a compression spring 146 is slipped over it and a retaining cap 154 is secured to the distal portion of the pin. The pin 150 is forceably moved by finger pressure and a portion of the dental floss 38 is wrapped around the exposed portion of the pin 150 under the head of the pin 150. Finger pressure is released and the pin 150 retracts due to the expansion of compressed spring 146 the floss 38 is positively secured to the rocker member 8'.

INDUSTRIAL APPLICABILITY

The body 6 and the rocker member 8 are preferably made from a durable plastic material such as LEXAN, a trademark of GE Plastic, Pittsfield, Mass. Ser. No. 72-323,698.

In operation, the handle 10 is formed to fit in the palm of the hand and is made to be reversible so that the distal portion 14 can extend upwardly or downwardly as well as being disposal in the right or left hand. In the dental flossing apparatus 4 of FIGS. 1-3 a new length of dental floss 38 is secured to first anchoring means 46, slipped through the contoured guide slots 60 of the blunted tines 18 and 20, and secured to the second anchoring means 48. Thereafter, two fingers are inserted in the opposing apertures 34 and 36 of the rocker member 8 and used to apply the desired amount of tension to the dental floss by manually urging the rocker member rearwardly or toward the handle. The coupling means 26 not only allows the rocker member 8 to slide back and forth on the shaft 12 a distance equal to the length of the elongate aperture 24, but also allows the rocker member to be pivoted relative thereto around the upright axis of the rivet 28. The two fingers, preferably the index and ring fingers, are thus used to control the tautness or stress in the floss. Simultaneously, these fingers can be pumped in opposition to each other to controllably pivot the rocker member 8 on the shaft 12 alternately in the clockwise and counterclockwise directions when viewing FIG. 1 to reciprocate the intermediate portion 44 of the dental floss between the tines 18 and 20.

Initially, the user can activate the switch 76 in the handle 10 to turn on the light bulb 78 and to illuminate the underside of the flosser head 14 prior to inserting the flosser head in the mouth. Whereupon the light allows the intermediate portion 44 of the dental floss 38 to be slipped more accurately into the interdental spaces between adjacent teeth. The cleaning or flossing action is greatly improved because the user can controllably pull back and/or pivot the rocker member with precise finger movement, as well as control the floss tension. In order to better see a particular problem areas between the rear teeth the user can temporarily snap the small mirror 120 onto the distal portion 14 of the shaft 12, and preferably while the light bulb 78 is lit.

The second embodiment dental flossing apparatus 4' shown in FIG. 4 operates in a similar manner, only the dental floss 38 is threaded from the spool assemblies 84 through the guide hooks 82 to the flosser head 14. If the floss becomes frayed it is a simple matter to manually raise the spool 106 with new floss therein away from the rocker member 8' so that the polygonal locking portion 114 of the spool shown in FIG. 5 disengaged from the fixed anchoring base 100 of the pin 98. The spool is manually raised against the resilient action of the coiled compression spring 108 which otherwise maintains the spool in a braked or locked-from-rotation mode. A length of new floss can then be easily unwound from the spool, thereupon that spool is released and allowed to relock. Thereafter the opposite spool is manually raised to allow it to be rotated and to take up the extra length of floss.

Alternate ways to retain floss are shown in FIGS. 11 and 12. In FIG. 11 finger pressure is applied to the retaining cap 148 to elevate the head of the pin 142 above the surface of the underlying rocker member 8' against the resiliency of the compression spring 146 whereby the indentation 144 is exposed. The first end of a length of floss 38 is then wrapped around or only slipped within the indentation 144 and the finger pressure is released whereby the floss 38 is retained. Although not illustrated, the second end of floss 38 is similarly attached to a like second floss anchoring pin 142. The floss anchoring pin 150 of FIG. 12 differs from the pin 142 of FIG. 11 in that the pin 150 has a multifaceted portion and the bore 152 matches the pin 150 configuration. The first end of a length of floss is again wrapped around the exposed portion of the pin 150 when finger pressure on the retaining cap 154 raises the pin. When finger pressure is released, the floss 38 is secured under the head of the retaining pin and against the multifacet edges.

It is also contemplated that the rocker member 8 need have only one arm 30 in engagement with the first end 40 of the dental floss 38 at the first anchoring means 46 as shown in FIG. 1, or at the left spool assembly 84 shown in FIG. 4. The second end 42 of the dental floss of such an arrangement can alternately be secured to an automatically tensioned, take-up spool, not shown, suitably connected to the body 6. In such an instance the pulling action of a single finger in the aperture 34 serves to pull the dental floss in opposition to the resilient action of the take-up spool. In this instance, the floss has a preselected degree of tension and can be reciprocated at will between the tines 18 and 20.

It is further contemplated that the rocker member 8 need not slide back and forth in the elongate aperture 24 as shown in FIG. 1 to provide for tensioning of the dental floss 38 but that the intermediate portion of the shaft 12 of the dental flossing apparatus 4 may be made in two telescoping parts 12' and 12" with a compression spring 15-6 therebetween as shown by the fragmentary view of the shaft in FIG. 13. When the first end 40 of the dental floss 38 is attached to the first anchoring means 46 and the second end 42 is attached to the second anchoring means 48, the floss is automatically tensioned by the compression spring carrying the distal portion away from the second part of the handle 10.

SUMMARY

In view of the foregoing, it can be appreciated that the dental flossing apparatus 48 of the present invention is easy to use and economical to produce. It takes up about the same space in the mouth as an average tooth brush, and yet can controllably allow reciprocating action of the dental floss across the slot 22 of the flosser head under the desired amount of tension by manipulation of the fingers of a single hand on the rocker member 8. Moreover, it provides an improved way of seeing precisely where the dental floss is relative to the space between adjacent teeth for improved manipulation thereof and improved cleaning of the teeth.

Other aspects, objects and advantages of this invention can be obtained from a study of the drawing, the disclosure, and the appended claims.

What is claimed is:

1. A dental flossing apparatus for controllably supporting in use a length of dental floss having first and second ends and an intermediate portion, comprising:
    a shaft having a gripping portion at one end thereof, a bifurcated distal portion defining a pair of tines at the other end thereof for spanningly receiving the intermediate portion of the floss, and an intermediate portion;
    a rocker member having first and second arms;
    anchoring means for connecting the first end of the floss to the first arm and the second end of the floss to the second arm; and
    coupling means for connecting the rocker member pivotally to the intermediate portion of the shaft so that the arms extend outwardly there form and allowing rocking movement thereof by the user and controlled reciprocation of the intermediate portion of the floss between the tines.

2. The dental flossing apparatus of claim 1 wherein the rocker member has a finger-receiving aperture in each of the arms, and the coupling means permits manual movement of the rocker member away from the distal portion of the shaft and controlled tensioning of the dental floss.

3. The dental flossing apparatus of claim 1 wherein the anchoring means includes a spool assembly mounted on each of the arms.

4. The dental flossing apparatus of claim 3 wherein at least one of the spool assemblies includes mounting means for allowing manual movement of its spool between a locked position and a freely rotatable position.

5. The dental flossing apparatus of claim 4 wherein the mounting means includes a pin connected to the respective arm; a spool on the pin, and locking means for selectively locking the spool to one end of the pin.

6. A dental flossing apparatus for controllably supporting in use a length of dental floss having first and second ends and an intermediate portion, comprising:
- an elongate body including a gripping portion, a distal portion defining a pair of tines and a slot therebetween, and an intermediate portion;
- a rocker member having a central part and first and second arms extending from the central part, the first and second arms being adapted to be connected to the first and second ends of the dental floss with the intermediate portion of the floss extending between the tines;
- first coupling means for pivotally connecting the central part of the rocker member to the intermediate portion of the body; and
- second coupling means for allowing separating movement between the rocker member and the distal portion of the body and thereby controlled tensioning of the dental floss.

7. The dental flossing apparatus of claim 6 wherein the second coupling means includes two separable parts of the intermediate portion of the body and a resilient spring element disposed therebetween, the separable parts being telescopically connected together.

8. The dental flossing apparatus of claim 6 including a delivery spool assembly connected to the first arm and adapted to be connected to the first end of the floss, and a receiving spool assembly connected to the second arm and adapted to be connected to the second end of the floss.

9. A dental flossing apparatus for cleaning teeth by controllably supporting a length of dental floss having first and second ends and an intermediate portion, comprising:
- an elongate body having a proximal gripping portion and a bifurcated distal portion defining a pair of tines and a slot therebetween, the tines including guiding means for retaining the intermediate portion of the floss so that it spans across the slot;
- a rocker member having an outstanding arm thereon;
- coupling means for pivotally connecting the rocker member to the body so that the arm extends outwardly from the body;
- first means mounted on the outstanding arm for pulling the first end of the floss in response to pivotal movement of the rocker member in a first direction on the body; and
- second means for reacting to the pulling of the first end of the floss at the second end thereof and for pulling the second end simultaneously with pivotal movement of the rocker member in a second direction opposite to the first direction, allowing reciprocating movement of the intermediate portion of the floss across the slot with reciprocating movement of the rocker member.

10. The dental flossing apparatus of claim 9 wherein the rocker member has another outstanding arm, the first means includes a first anchoring device mounted on the outstanding arm, and the second means includes a second anchoring device mounted on the another outstanding arm.

11. The dental flossing apparatus of claim 10 wherein the rocker member has a finger-receiving aperture in each arm.

12. The dental flossing apparatus of claim 10 wherein the coupling means includes an elongate aperture in the body and the rocker member is adapted to slide therein toward and away from the bifurcated distal portion, and to pivot relative thereto.

13. The dental flossing apparatus of claim 10 wherein the body includes a shaft with the bifurcated distal portion defined thereon, and the gripping portion includes a handle disposed substantially perpendicular to the shaft to form a T-shape therewith.

14. The dental flossing apparatus of claim 10 wherein the first anchoring device includes a bore through the outstanding arm, an anchoring pin receivable in the bore and having an indentation therein and a head, a compression spring, and a retaining cap, for receiving the dental floss being received in the indentation with the compression spring retracting against the outstanding arm and urging the head of the pin in a direction for securing the floss in a locked state within the bore.

15. The dental flossing apparatus of claim 10 wherein the second anchoring device includes a multifaceted bore through the another outstanding arm, a multifaceted anchoring pin receivable in the multifaceted bore and having a head, a compression spring, and a retaining cap, for receiving the dental floss around the multifaceted pin with the compression spring retracting against the another outstanding arm and urging the pin in a direction for securing the floss in a locked state under the retaining cap.

16. The dental flossing apparatus of claim 10 wherein the first and second anchoring devices include cleats.

17. The dental flossing apparatus of claim 10 wherein the coupling means includes means for allowing manually imposed movement of the rocker member away from the distal portion to impart controlled tensioning of the dental floss.

18. The dental flossing apparatus of claim 9 wherein the first means includes a spool assembly for receiving the dental floss wrappingly therearound.

19. The dental flossing apparatus of claim 18 wherein the spool assembly has a pin, a spool mounted on the pin, and connecting means permitting selected movement of the spool between locked and unlocked positions on the pin.

20. The dental flossing apparatus of claim 9 wherein the body includes a shaft having a flattened intermediate portion and wherein the rocker member is relatively flat and engageable with the flattened intermediate portion for stability when rocked.

21. The dental flossing apparatus of claim 9 wherein the guiding means includes an aperture across each of the tines.

22. The dental flossing apparatus of claim 21 wherein the guiding means includes a zig-zag slit at the forward end of each tine, the zig-zag slit intersecting with its respective aperture.

23. The dental flossing apparatus of claim 21 wherein the guiding means includes a beveled straight slit at the forward end of each tine, the beveled straight slit intersecting with its respective aperture.

24. The dental flossing apparatus of claim 21 wherein the guiding means includes a diagonal slit at the forward end of each tine, the diagonal slit intersecting with its respective aperture.

25. The dental flossing apparatus of claim 9 wherein the second means includes an automatically tensioned take-up spool connected to the body.

26. The dental flossing apparatus of claim 9 including further means for allowing separating movement between the rocker member and the distal portion of the body and thereby controlled tensioning of the dental floss.

* * * * *